United States Patent
Salo et al.

(10) Patent No.: US 8,560,067 B2
(45) Date of Patent: Oct. 15, 2013

(54) APPARATUS FOR SPATIALLY AND TEMPORALLY DISTRIBUTING CARDIAC ELECTRICAL STIMULATION

(75) Inventors: Rodney W. Salo, Fridley, MN (US); Julio C. Spinelli, Shoreview, MN (US); Bruce H. KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1370 days.

(21) Appl. No.: 11/931,779

(22) Filed: Oct. 31, 2007

(65) Prior Publication Data
US 2008/0097538 A1    Apr. 24, 2008

Related U.S. Application Data

(63) Continuation of application No. 10/634,232, filed on Aug. 5, 2003, now Pat. No. 7,292,887, which is a continuation of application No. 09/544,363, filed on Apr. 6, 2000, now Pat. No. 6,640,135.

(51) Int. Cl.
*A61N 1/368* (2006.01)

(52) U.S. Cl.
USPC .............. 607/6; 607/4; 607/5; 607/9; 607/15; 607/17; 607/20

(58) Field of Classification Search
None
See application file for complete search history.

(56) References Cited

U.S. PATENT DOCUMENTS

| | | |
|---|---|---|
| 3,606,882 A | 9/1971 | Zenmon, Abe et al. |
| 4,354,497 A | 10/1982 | Kahn |
| 4,549,548 A | 10/1985 | Wittkampf et al. |
| 4,554,922 A | 11/1985 | Prystowsky et al. |
| 4,628,934 A | 12/1986 | Pohndorf et al. |
| 4,674,518 A | 6/1987 | Salo |
| 4,686,987 A | 8/1987 | Salo et al. |
| 4,872,459 A | 10/1989 | Pless et al. |
| 4,880,005 A | 11/1989 | Pless et al. |
| 4,928,688 A | 5/1990 | Mower |
| 5,003,975 A | 4/1991 | Hafelfinger et al. |
| 5,014,698 A | 5/1991 | Cohen |
| 5,058,605 A | 10/1991 | Slovak |

(Continued)

FOREIGN PATENT DOCUMENTS

| | | |
|---|---|---|
| EP | 0522693 A1 | 1/1993 |
| WO | WO-9725098 A1 | 7/1997 |

(Continued)

OTHER PUBLICATIONS

"U.S. Appl. No. 09/544,363, Notice of Allowance mailed Mar. 24, 2003", 4 pgs.

(Continued)

*Primary Examiner* — Kennedy Schaetzle
(74) *Attorney, Agent, or Firm* — Schwegman Lundberg & Woessner, P.A.

(57) ABSTRACT

A cardiac electro-stimulatory device and method for operating same in which stimulation pulses are distributed among a plurality of electrodes fixed at different sites of the myocardium in order to reduce myocardial hypertrophy brought about by repeated pacing at a single site and/or increase myocardial contractility. In order to spatially and temporally distribute the stimulation, the pulses are delivered through a switchable pulse output configuration during a single cardiac cycle, with each configuration comprising one or more electrodes fixed to different sites in the myocardium.

20 Claims, 1 Drawing Sheet

(56) References Cited

U.S. PATENT DOCUMENTS

| | | |
|---|---|---|
| 5,109,842 A | 5/1992 | Adinolfi |
| 5,156,149 A | 10/1992 | Hudrlik |
| 5,158,079 A | 10/1992 | Adams et al. |
| 5,174,289 A | 12/1992 | Cohen |
| 5,233,985 A | 8/1993 | Hudrlik |
| 5,267,560 A | 12/1993 | Cohen |
| 5,340,361 A | 8/1994 | Sholder |
| 5,344,386 A | 9/1994 | Schaldach |
| 5,370,665 A | 12/1994 | Hudrlik |
| 5,507,782 A | 4/1996 | Kieval et al. |
| 5,514,161 A | 5/1996 | Limousin |
| 5,534,016 A | 7/1996 | Boute |
| 5,584,867 A | 12/1996 | Limousin et al. |
| 5,674,259 A | 10/1997 | Gray |
| 5,683,429 A | 11/1997 | Mehra |
| 5,707,398 A | 1/1998 | Lu |
| 5,738,096 A | 4/1998 | Ben-Haim |
| 5,749,906 A | 5/1998 | Kieval et al. |
| 5,782,774 A | 7/1998 | Shmulewitz |
| 5,792,203 A | 8/1998 | Schroeppel |
| 5,797,970 A | 8/1998 | Pouvreau |
| 5,800,464 A | 9/1998 | Kieval |
| 5,824,019 A | 10/1998 | Rueter et al. |
| 5,851,226 A | 12/1998 | Skubitz et al. |
| 5,935,160 A | 8/1999 | Auricchio et al. |
| 5,995,870 A | 11/1999 | Cazeau et al. |
| 5,995,871 A | 11/1999 | Knisley |
| 6,038,483 A | 3/2000 | KenKnight et al. |
| 6,058,329 A | 5/2000 | Salo et al. |
| 6,066,094 A | 5/2000 | Ben-Haim |
| 6,112,116 A | 8/2000 | Fischell et al. |
| 6,112,117 A | 8/2000 | KenKnight et al. |
| 6,151,524 A | 11/2000 | Krig et al. |
| 6,152,955 A | 11/2000 | KenKnight et al. |
| 6,223,082 B1 | 4/2001 | Bakels et al. |
| 6,285,898 B1 | 9/2001 | Ben-Haim |
| 6,285,906 B1* | 9/2001 | Ben-Haim et al. ............ 607/4 |
| 6,292,693 B1 | 9/2001 | Darvish et al. |
| 6,314,322 B1 | 11/2001 | Rosenberg |
| 6,317,631 B1 | 11/2001 | Ben-Haim et al. |
| 6,363,279 B1 | 3/2002 | Ben-Haim et al. |
| 6,418,340 B1 | 7/2002 | Conley et al. |
| 6,418,343 B1 | 7/2002 | Zhang et al. |
| 6,507,756 B1 | 1/2003 | Heynen et al. |
| 6,556,872 B2 | 4/2003 | Hauck |
| 6,574,506 B2 | 6/2003 | Kramer et al. |
| 6,628,988 B2 | 9/2003 | Kramer et al. |
| 6,640,135 B1 | 10/2003 | Salo et al. |
| 6,868,287 B1 | 3/2005 | Rosen et al. |
| 6,915,160 B2 | 7/2005 | Auricchio et al. |
| 6,965,797 B2 | 11/2005 | Pastore et al. |
| 6,973,349 B2 | 12/2005 | Salo |
| 7,065,405 B2 | 6/2006 | Pastore et al. |
| 7,103,410 B2 | 9/2006 | Kramer et al. |
| 7,158,824 B2 | 1/2007 | Girouard et al. |
| 7,215,997 B2 | 5/2007 | Yu et al. |
| 7,292,887 B2 | 11/2007 | Salo et al. |
| 7,295,874 B2 | 11/2007 | Prinzen et al. |
| 7,346,394 B2 | 3/2008 | Liu et al. |
| 7,346,397 B2 | 3/2008 | Money et al. |
| 7,437,191 B2 | 10/2008 | Pastore et al. |
| 7,548,782 B2 | 6/2009 | Kramer et al. |
| 7,676,259 B2 | 3/2010 | Auricchio et al. |
| 8,046,066 B2 | 10/2011 | Kramer et al. |
| 2002/0002389 A1 | 1/2002 | Bradley et al. |
| 2002/0045809 A1 | 4/2002 | Ben-Haim |
| 2002/0082647 A1 | 6/2002 | Alferness et al. |
| 2002/0115081 A1 | 8/2002 | Lee et al. |
| 2003/0023278 A1 | 1/2003 | Pastore et al. |
| 2003/0105493 A1 | 6/2003 | Salo |
| 2004/0030357 A1 | 2/2004 | Salo et al. |
| 2004/0044374 A1 | 3/2004 | Weinberg et al. |
| 2004/0049236 A1 | 3/2004 | Kramer et al. |
| 2004/0054381 A1 | 3/2004 | Pastore et al. |
| 2005/0065568 A1 | 3/2005 | Liu et al. |
| 2005/0177195 A1 | 8/2005 | Salo |
| 2005/0216066 A1 | 9/2005 | Auricchio et al. |
| 2006/0293716 A1 | 12/2006 | Kramer et al. |
| 2008/0097541 A1 | 4/2008 | Salo et al. |
| 2009/0254141 A1 | 10/2009 | Kramer et al. |

FOREIGN PATENT DOCUMENTS

| | | |
|---|---|---|
| WO | WO-99/10042 A1 | 3/1999 |
| WO | WO-00/09206 A1 | 2/2000 |
| WO | WO-0004947 A2 | 2/2000 |
| WO | WO-0108748 A1 | 2/2001 |
| WO | WO-0108748 A2 | 2/2001 |
| WO | WO-0130436 A2 | 5/2001 |
| WO | WO-01/76689 A1 | 10/2001 |
| WO | WO-02087694 A1 | 11/2002 |

OTHER PUBLICATIONS

"U.S. Appl. No. 09/544,363, Non-Final Office Action mailed Aug. 29, 2002", 6 pgs.

"U.S. Appl. No. 09/544,363, Response filed Dec. 17, 2002 to Non-Final Office Action mailed Aug. 29, 2002", 8 pgs.

"U.S. Appl. No. 10/634,232, Amendment and Response filed Apr. 4, 2007 to Non-Final Office Action mailed Jan. 4, 2007", 9 pgs.

"U.S. Appl. No. 10/634,232, Non-Final Office Action mailed Jan. 4, 2007", 6 pgs.

"U.S. Appl. No. 10/634,232, Non-Final Office Action mailed Jul. 5, 2006", 5 pgs.

"U.S. Appl. No. 10/634,232, Notice of Allowance mailed Jun. 27, 2007", 7 pgs.

"U.S. Appl. No. 10/634,232, Response filed Oct. 5, 2006 to Non-Final Office Action mailed Jul. 5, 2006", 9 pgs.

"European Application Serial No. 01931123.2, Communication mailed Mar. 10, 2003", 4 pgs.

"European Application Serial No. 01931123.2, Communication mailed Oct. 28, 2003'", 1 pg.

"European Application Serial No. 01931123.2, Response filed Jan. 6, 2004 to Communications mailed Oct. 28, 2003 and Mar. 10, 2003", 9 pgs.

"International Application Serial No. PCT/US01/40415, International Preliminary Report mailed Jul. 4, 2002", 3 pgs.

"International Application Serial No. PCT/US01/40415, International Search Report mailed Oct. 19, 2001", 2 pgs.

"International Application Serial No. PCT/US01/40415, Written Opinion mailed Apr. 10, 2002", 2 pgs.

Braunwald, N. S, et al., "Sustained Paired Electrical Stimuli; Slowing of the Ventricular Rate and Augmentation of Contractile Force", *American Journal of Cardiology*, 14, (1964), 385-393.

Sabbah, H. N, et al., "Delivery of Non-Excitatory Contractility-Modulation Electic Signals Improve Left Ventricular Performance in Dogs with Heart Failure", *Circulation, Supplement 1*, 100 (18), Abstract No. 631, (Nov. 2, 1999), pp. I-122.

"U.S. Appl. No. 11/135,191, Notice of Allowance mailed Oct. 21, 2009", 5 pgs.

"U.S. Appl. No. 11/135,191, Response filed Jun. 18, 2009 to Non Final Office Action mailed Mar. 18, 2009", 8 pgs.

"U.S. Appl. No. 11/931,718, Non-Final Office Action mailed Jun. 25, 2010", 10 pgs.

"European Application Serial No. 03737691.0, Office Action mailed Aug. 14, 2009", 4 pgs.

"International Application Serial No. PCT/US02/12850, International Search Report mailed Aug. 16, 2002", 3 pgs.

"International Application Serial No. PCT/US03/03659, International Search Report mailed Aug. 22, 2003", 7 pgs.

Holt, J. H., et al., "A Study of the Human as a Multiple Dipole Electrical Source:III. Diagnosis and Quantitation of Right Ventricular Hypertrophy", Circulation, 40(5), (1969), 711-718.

Okin, P. M, et al., "Time-Voltage QRS Area of the 12-Lead Electrocardiogram:Detection of Left Ventricular Hypertrophy", Hypertension, 31(4), (Apr. 1998), 937-942.

Vakili, B. A, et al., "Prognostic implications of left ventricular hypertrophy", American Heart Journal, 141(3), (Mar. 2001), 334-341.

(56) References Cited

OTHER PUBLICATIONS

"U.S. Appl. No. 11/931,718, Notice of Allowance mailed Sep. 2, 2011", 7 pgs.
"U.S. Appl. No. 12/484,882, Notice of Allowance mailed Jun. 27, 2011", 5 pgs.
"U.S. Appl. No. 12/484,882, Response filed Apr. 19, 2011 to Non Final Office Action mailed Jan. 19, 2011", 11 pgs.
"U.S. Appl. No. 09/84,4256, Notice of Allowance mailed May 7, 2003", 8 pgs.
"U.S. Appl. No. 09/844,256, Non-Final Office Action mailed Jan. 14, 2003", 6 pgs.
"U.S. Appl. No. 09/844,256, Response filed Apr. 14, 2003 to Non-Final Office Action mailed Jan. 14, 2003", 7 pgs.
"U.S. Appl. No. 10/005,184, Non-Final Office Action mailed Feb. 17, 2005", 6 pgs.
"U.S. Appl. No. 10/005,184, Non Final Office Action mailed Mar. 24, 2004", 4 pgs.
"U.S. Appl. No. 10/005,184, Notice of Allowance mailed Jul. 19, 2005", 5 pgs.
"U.S. Appl. No. 10/005,184, Notice of Allowance mailed Sep. 10, 2004", 5 pgs.
"U.S. Appl. No. 10/005,184, Response filed May 17, 2005 to Non-Final Office Action mailed Feb. 17, 2005", 7 pgs.
"U.S. Appl. No. 10/005,184, Response filed Jul. 26, 2004 to Non Final Office Action mailed Mar. 24, 2004", 8 pgs.
"U.S. Appl. No. 10/071,875, Notice of Allowance mailed Feb. 9, 2005", 6 pgs.
"U.S. Appl. No. 10/071,875, Notice of Allowance mailed Sep. 27, 2004", 6 pgs.
"U.S. Appl. No. 10/244,089, Non-Final Office Action mailed Dec. 23, 2004", 7 pgs.
"U.S. Appl. No. 10/244,089, Notice of Allowance mailed Jun. 17, 2005", 7 pgs.
"U.S. Appl. No. 10/244,089, Response filed Mar. 23, 2005 to Non-Final Office Action mailed Dec. 23, 2004", 8 pgs.
"U.S. Appl. No. 10/649,468, Non Final Office Action mailed Aug. 29, 2005", 7 pgs.
"U.S. Appl. No. 10/649,468, Notice of Allowance mailed Mar. 1, 2006", 6 pgs.
"U.S. Appl. No. 10/649,468, Response filed Nov. 29, 2005 to Non Final Office Action mailed Aug. 29, 2005", 10 pgs.
"U.S. Appl. No. 11/025,847, Non-Final Office Action mailed Oct. 9, 2007", 4 pgs.
"U.S. Appl. No. 11/135,191, Advisory Action mailed Dec. 24, 2008", 3 pgs.
"U.S. Appl. No. 11/135,191, Final Office Action mailed Sep. 8, 2008", 7 pgs.
"U.S. Appl. No. 11/135,191, Non Final Office Action mailed Mar. 18, 2009", 7 pgs.
"U.S. Appl. No. 11/135,191, Non-Final Office Action mailed Mar. 3, 2008", 5 pgs.
"U.S. Appl. No. 11/135,191, Response filed Jun. 3, 2008 to Non-Final Office Action mailed Mar. 3, 2008", 9 pgs.
"U.S. Appl. No. 11/135,191, Response filed Nov. 10, 2008 to Final Office Action mailed Sep. 8, 2008", 7 pgs.
"U.S. Appl. No. 11/469,620, Final Office Action mailed Nov. 17, 2008", 6 pgs.
"U.S. Appl. No. 11/469,620, Notice of Allowance mailed Feb. 10, 2009", 4 pgs.
"U.S. Appl. No. 11/469,620, Response filed Jan. 21, 2009 to Final Office Action mailed Jan. 17, 2008", 7 pgs.
"U.S. Appl. No. 11/469,620, Response filed Jul. 11, 2008 to Non-Final Office Action mailed Apr. 11, 2008", 13 pgs.
"U.S. Appl. No. 11/469,620 Non-Final Office Action mailed Apr. 11, 2008", 12 pgs.
"U.S. Appl. No. 11/931,718, Notice of Allowance mailed Dec. 8, 2010", 4 pgs.
"U.S. Appl. No. 11/931,718, Response filed Sep. 27, 2010 to Non Final Office Action mailed Jun. 25, 2010", 9 pgs.
"U.S. Appl. No. 12/484,882, Non Final Office Action mailed Jan. 19, 2011", 6 pgs.
Reiter, M. J., et al., "Electrophysiological Effects of Acute Dilatation in the Isolated Rabbit Hear", Circulation, 96(11), (Dec. 2, 1997), 4050-4056.
Watanabe, M., et al., "Developmental Remodeling and Shortening of Cardiac Outflow Tract Involves Myocyte Programmed Cell Death", Development, 125(19), (1998), 3809-3820.

\* cited by examiner

APPARATUS FOR SPATIALLY AND TEMPORALLY DISTRIBUTING CARDIAC ELECTRICAL STIMULATION

CROSS-REFERENCE TO RELATED APPLICATION(S)

This application is a continuation of U.S. patent application Ser. No. 10/634,232, filed on Aug. 5, 2003 and published as US 2004/0030357, now issued as U.S. Pat. No. 7,292,887, which is a continuation of U.S. patent application Ser. No. 09/544,363, filed on Apr. 6, 2000, now issued as U.S. Pat. No. 6,640,135, the specifications of which are incorporated herein by reference.

FIELD OF THE INVENTION

This invention pertains to apparatus and methods for electrostimulation of the heart including cardiac pacing with an artificial pacemaker. In particular, the invention relates to the manner in which electrical stimulation is delivered to the heart.

BACKGROUND

Conventional cardiac pacing with implanted pacemakers involves excitatory electrical stimulation of the heart by an electrode in electrical contact with the myocardium. (As the term is used herein, "excitatory stimulation" refers to stimulation intended to cause a cardiac contraction.) The pacemaker is usually implanted subcutaneously on the patient's chest, and is connected to an electrode for each paced heart chamber by leads threaded through the vessels of the upper venous system into the heart. In response to sensed electrical cardiac events and elapsed time intervals, the pacemaker delivers to the myocardium a depolarizing voltage pulse of sufficient magnitude and duration to cause an action potential. A wave of depolarizing excitation then propagates through the myocardium, resulting in a heartbeat.

The normal rhythmic impulse of the heart is first generated in pacemaker tissue known as the sino-atrial (SA) node, spreads throughout the atria causing atrial contraction, and is then conducted to the atrioventricular (AV) node where the impulse is delayed before passing into the ventricles. The ventricles of a normal heart are then electrically stimulated by excitation emanating from the AV node that spreads to the heart via specialized conduction pathways known as Purkinje fibers. These fibers lie beneath the endocardium and spread throughout each ventricular chamber where they penetrate into the myocardium and become continuous with the muscle fibers. The conduction velocity of the Purkinje fibers is very rapid so that the time between the impulse leaving the AV node and spreading to the entire endocardial surface of the ventricles is only approximately 0.03 seconds. Once the impulse has reached the ends of the Purkinje fibers, it is then transmitted through the ventricular muscle mass by the muscle fibers themselves with a conduction velocity only about one-sixth that of the Purkinje fibers. Because of the rapid excitation of the entire endocardial surface by the Purkinje system, however, the spread of excitation from the endocardial surface to the epicardial surface of the ventricles takes only about another 0.03 seconds. This means that in the normal heart, excitation of the first ventricular muscle fiber occurs only about 0.06 seconds before the last ventricular muscle fiber is excited. The result is a synchronous contraction in which all portions of the ventricular muscle in both ventricles begin contracting at nearly the same time. Not only does this increase the pumping efficiency of the ventricles, but it also evenly distributes ventricular wall stress during the pumping cycle.

Unfortunately, artificial ventricular pacing with an electrode fixed into an area of the myocardium cannot take advantage of the heart's normal Purkinje conduction system because that system can only be entered by impulses emanating from the AV node. Thus the spread of excitation must proceed only via the much slower conducting ventricular muscle fibers, resulting in the part of the ventricular myocardium stimulated by the pacing electrode contracting well before parts of the ventricle located more distally to the electrode. Although the pumping efficiency of the heart is somewhat reduced from the optimum, most patients can still maintain more than adequate cardiac output with artificial pacing.

Another deleterious effect of the conduction delays brought about by artificial pacing, however, is the uneven distribution of wall stress during the cardiac pumping cycle. The degree of tension on a heart muscle fiber before it begins to contract is termed the preload. Because pressure within the ventricles rises rapidly from a diastolic to a systolic value as blood is pumped out into the aorta and pulmonary arteries, the part of the ventricle that first contracts due to a pacing pulse does so against a lower pressure preload than does a part of the ventricle contracting later which unevenly stresses the myocardium. The heart's physiological response to this uneven preload and stress is compensatory hypertrophy in the areas of the myocardium that must contract against a greater pressure load. Not only can this hypertrophy cause blood flow problems that may further hinder pumping efficiency, but it has been found that myocytes (i.e., cardiac muscle cells) which are made to contract against a greater than normal mechanical load can be induced to undergo apoptosis (i.e., genetically programmed cell death). This may be especially true in pacemaker patients, a large proportion of whom do not have healthy myocardium to begin with, most commonly as a result of ischemic heart disease.

SUMMARY OF THE INVENTION

The present invention is a method and apparatus for cardiac stimulation that spatially and temporally distributes electrical stimulation to more than one site of either the atria or ventricles. One embodiment involves distributing excitatory electrical stimulation for pacing the heart with an artificial pacemaker. A primary objective in distributing the pacing to multiple sites is to reduce disparities in the distribution of preload and stress during systole to thereby reduce compensatory hypertrophy of the myocardium and/or apoptosis of myocytes. In one embodiment, a plurality of pacing electrodes are fixed at separate sites, and a selected electrode or group of electrodes among the plurality are energized during any one cardiac cycle. The selected electrode or electrodes used to stimulate the heart chamber may then be switched to a different electrode or group of electrodes on a beat-to-beat basis, at fixed time intervals, or in accordance with a sensed parameter. A particular mode of practicing the invention can also be implemented with a conventional pacemaker having a single bipolar pacing electrode for pacing a particular heart chamber and control circuitry for changing the polarity of the electrode in accordance with a switching algorithm.

In another embodiment, non-excitatory electrical stimulation is distributed over the myocardium similar to the distributed pacing described above. In this case, however, rather than pacing the heart, the stimulation is employed to enhance myocardial contractility by delivering stimulatory electrical pulses synchronized with intrinsic cardiac activity and during the myocardial refractory period. Such stimulation may be delivered either by a specialized electro-stimulatory device or a pacemaker configured to deliver non-excitatory stimulation to the heart.

DESCRIPTION OF THE INVENTION

Figure 1:
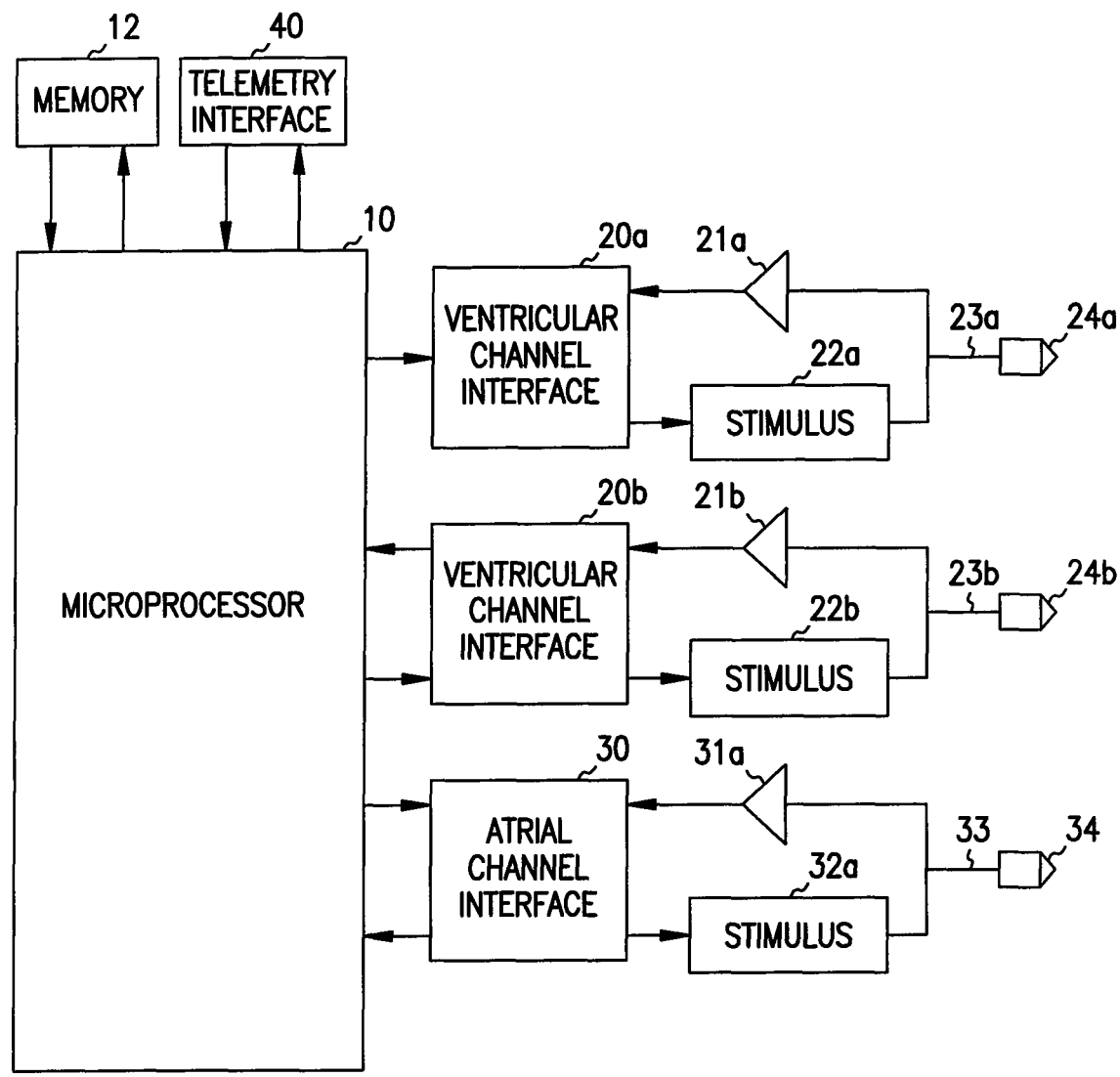
FIG. 1 is a block diagram of an exemplary electro-stimulatory cardiac device for practicing the present invention.

In accordance with the invention, an electro-stimulatory device spatially and temporally distributes stimulatory pulses to multiple sites of either the atria or ventricles by switching between different electrode configurations. Such electro-stimulatory devices include both devices for pacing the heart with excitatory stimulation (i.e., artificial pacemakers) as well as devices for delivering non-excitatory stimulation pulses to the heart. Furthermore, the term should be taken to include any cardiac rhythm management device, such as an implantable cardioverter/defibrillator, with a pacing or non-excitatory stimulation function incorporated therein.

Pacemakers have been constructed for delivering pacing pulses to multiple ventricular or atrial sites, including so-called biventricular pacemakers where pacing pulses are delivered to both ventricles by separate electrodes during a cardiac cycle. (See, e.g., U.S. Pat. Nos. 5,792,203 and 4,928,688, referred to herein as the '203 and '688 patents, which are hereby incorporated by reference.) One type of multi-site pacing involves fixing two or more pacing electrodes to separate sites of the same heart chamber, either an atrium or a ventricle. For example, one electrode may be fixed to the apical region of either the right or left ventricle with the other electrode fixed to a basal region of the same ventricle. In the case of the left ventricle, this may be most easily accomplished by using a coronary sinus lead (See U.S. Pat. No. 5,935,160, hereby incorporated by reference) with distal and proximal electrodes. The ventricle can be paced in accordance with a programmed pacing mode with the electrodes being energized simultaneously during each pacing output in order to achieve near simultaneous activation of the ventricle. Alternatively, the pacing stimuli can be delivered to the ventricular electrodes sequentially with a specified time delay in order to take into account differing conduction times within the ventricle.

Biventricular pacemakers, such as described in the '688 patent, provide pacing to both ventricles in the presence of an interventricular conduction defect. Biventricular pacing may also be useful in certain instances, however, when interventricular conduction pathways are intact. For example, a biventricular pacemaker of the kind described in the '688 patent can be configured with one electrode pacing the posterior or lateral wall of the left ventricle and the other electrode pacing the apex of the right ventricle. When only the left ventricular site is paced, the spread of activation is from the paced site as well as from the part of the normal left ventricular conduction system that is still intact (which would be in the vicinity of the basal region of the interventricular septum). Thus, although only one site is paced, the spread of activation is from two sites. If, on the other hand, both sites are paced, either simultaneously or with a specified interventricular delay between the right and left ventricles, a similar spread of activation occurs from the left ventricular site, but a changed activation occurs from the right ventricular site that breaks through into the left ventricle somewhere in the apical region of the interventricular septum. There is thus left ventricular activation spreading from two (or more) sites which is different from the activation that occurs with left ventricular pacing alone. By adjusting the interventricular delay, the relative spread of activation between the two pacing sites can be modified which thereby affects the wall stress developed near these sites and throughout the ventricle during contraction.

Multi-site pacemakers such as described in the '688 and '203 patents are capable of delivering pacing stimuli to multiple sites of the atria or ventricles in which the multiple sites are all stimulated during any one cardiac cycle. Each of the pulses delivered to the multiple pacing sites during the cardiac cycle, however, must be of sufficient energy (i.e., sufficient pulse amplitude and duration) to cause heart muscle contraction were it to be delivered alone, since pacing stimuli applied over a wide area cannot sum together. Both because of increased battery requirements and the physiological effects on the heart, therefore, it may not be desirable to deliver simultaneous pacing at multiple sites. Furthermore, certain patients may benefit from activating parts of the ventricle at different times in order to distribute the pumping load to different areas of the ventricle. For example, a relatively weak area of the myocardium could be activated before stronger areas to result in a distribution of wall stress that increases pumping efficiency. In any of the situations discussed above, therefore, it may be desirable to spatially and temporally distribute the pacing. In accordance with the invention, a multi-site pacemaker accomplishes this objective by switching the output of pacing pulses between selected electrodes or groups of electrodes during different cardiac cycles.

Another useful application of spatial/temporal switching is to distribute the effects of localized multi-site stimulation pulses that can improve myocardial contractility. (See Braunwald et al., *Sustained paired electrical stimuli; Slowing of the ventricular rate and augmentation of contractile force*, American Journal of Cardiology 14:385, 1964; Sabbah, et al., *Delivery of Non-excitatory Contractility-Modulation Electric Signals Improve Left Ventricular Performance in Dogs with Heart Failure*, Circulation Supplement 1, Vol. 100, pg. I-122, Abstract 631, Nov. 2, 1999). In this type of pacing, multiple pulses are output to a pacing electrode during one or more phases of the action potential in order to improve local contractile function. For example, a non-excitatory stimulating pulse could be applied after a pacing pulse and during the absolute refractory period to increase intracellular calcium concentration which thereby enhances contractility. Because this type of stimulation also increases local oxygen consumption, switching the stimulation site by spatially and temporally distributing the stimulation in accordance with the present invention serves to help prevent deleterious effects at the pacing site. Such effects may be due to biological adaptation resulting from expression of intracellular proteins involved in ion transport and contractile function.

Cardiac pacemakers stimulate the heart by delivering a voltage pulse to an electrode situated on or in the myocardium, with the stimulating electrode usually acting as a cathode. The electrode may be "fixed" to a heart chamber in one of three basic ways: it may be left to float inside one of the heart chambers near the heart wall, actively fixed in the myocardium by implantation, or passively fixed against the endocardium via a tissue encapsulation reaction. In order to pace the heart, the electrode must deliver a voltage pulse of sufficient magnitude and duration to cause a propagated action potential resulting in a contraction of the myocardium (i.e., an excitatory stimulation). In accordance with the invention, pacing is delivered to a heart chamber through a switchable configuration of pacing electrodes, wherein a pulse output configuration is defined as a specific subset of a plurality of electrodes fixed to the paced chamber and to which pacing pulses are applied. A plurality of different pulse output configurations may be defined as subsets of electrodes that can be selected for pacing. By switching the pulse output configuration to a different configuration, pacing to the heart chamber is thereby temporally distributed among the total number of fixed electrodes. For example, two electrodes may be fixed to a heart chamber with each electrode constituting a pulse output configuration, and switching the pulse output configuration alternately between the electrodes.

In various embodiments of the invention, a particular electro-stimulatory configuration may comprise one or more electrodes, and a particular electrode may belong to one or more configurations. A plurality of different pulse output configurations may then be defined as subsets of the total number of stimulatory (for pacing or non-excitatory stimulation) electrodes fixed to the paced heart chamber. For example, the pacemaker may have N ventricular stimulatory electrodes with a particular subset n of those electrodes selected for pacing in a particular pulse output configuration, so that stimuli are applied to n different sites in the ventricle during a cardiac cycle. In accordance with a particular switching algorithm, the pulse output configuration may then be switched to a different subset m of the N channels to spatially and temporally distribute the stimulation. The subset m making up the configuration that is switched to may be any combination of the N electrodes. That is, the number of electrodes in the subset m may be the same or different as the number of electrodes in the subset n, and the two subsets may have electrodes in common. A pulse output configuration may also be further defined as a particular temporal sequence of pacing or non-excitatory stimulation pulses applied to the electrodes making up the configuration. For example, a pulse output configuration may consist of two electrodes fixed to separate sites of a heart chamber, and the heart chamber is paced (or otherwise stimulated) by applying a pulse to one electrode and then the other after a specified time delay.

The present invention may be applied to distribute the pacing or non-excitatory stimulation of a heart chamber where the stimulated chamber may be either the atria or ventricles, or both. Furthermore, since the atria and ventricles both consist of paired chambers (i.e., right/left ventricle or atrium), the electrodes may be fixed to the stimulated chamber in a number of different ways. For example, in one embodiment, a ventricular pacemaker (or other electro-stimulatory device) has a set of pulse output configurations with each configuration comprising electrodes fixed to a single ventricle. In another embodiment, the available configurations may comprise electrodes fixed to both ventricles. In still another embodiment, each configuration is confined to one ventricle, but configurations are available for each ventricle so that stimulation pulses can be applied to either ventricle.

Pacing or non-excitatory stimulation may be distributed over the myocardium of a heart chamber by switching between pulse output configurations according to a switching algorithm. Switching between pulse output configurations can be made to occur on a beat-to-beat basis so that the stimulated site is alternated on every cardiac cycle or multiples of cycles. Alternatively, the configurations can be switched at periodic time intervals so that the pacing site is changed either rapidly (e.g., every minute) or over a much longer time period (e.g., weekly, monthly, etc.) depending upon the needs of the patient. The switching may also performed in accordance with a sensed physiological parameter so that the pulse output configuration is switched when the variable falls outside of a specified range. In one embodiment, cardiac output (as determined by, e.g., impedance measurement as described in U.S. Pat. No. 4,674,518 issued to Salo et al., the disclosure of which is hereby incorporated by reference) is monitored, and the pulse output configuration is switched if it falls below a specified value. In another implementation, the depolarization following a pacing pulse is sensed at one or more sites at some distance from the pacing site or sites, and the time delay between the pacing pulse and the sensed depolarization is measured. The pulse output configuration is then switched if the time delay exceeds a specified value. In another embodiment, the mean or minimum heart rate is monitored (e.g., for a 24 hour period) and the pulse output configuration is switched if the rate exceeds a threshold value. The specified parameter values used for switching the pulse output configuration is preferably programmable to suit the needs of individual patients. The change in the sensed physiological parameter that results when a particular pulse output configuration is switched on may also be used to select the best pulse output configuration. The device may be programmed to go through a testing sequence in which pulse output configurations are alternately switched on and off, with the pulse output configuration then selected in accordance with which one produces the greatest improvement in the sensed parameter. For example, the pulse output configuration that produces the highest cardiac output, the shortest measured time delay, or the lowest mean or minimum heart rate may be selected for pacing. Lastly, it may be desirable in some patients to simply configure the pacemaker to use only one pulse output configuration and switch to another configuration at a discretionary time using a telemetry interface.

A block diagram of a cardiac electro-stimulatory device having two ventricular stimulation channels is shown in FIG. 1. The control unit of the pacemaker is made up of a microprocessor 10 communicating with a memory 12 via a bidirectional data bus 13, where the memory 12 typically comprises a ROM (read-only memory) for program storage and a RAM (random-access memory) for data storage. The control unit could also include dedicated circuitry either instead of, or in addition to, the programmed microprocessor for controlling the operation of the device. The control unit is capable of operating the device in a number of programmed modes where a programmed mode defines how pulses are output in response to sensed events and expiration of time intervals. A telemetry interface 40 is also provided for communicating with an external programmer.

The pacemaker has atrial sensing/stimulation channels comprising electrode 34, lead 33, sensing amplifier 31, pulse generator 32, and an atrial channel interface 30 which communicates bidirectionally with a port of microprocessor 10. The device also has two ventricular sensing/stimulation channels that include electrodes 24a-b, leads 23a-b, sensing amplifiers 21a-b, pulse generators 22a-b, and ventricular channel interfaces 20a-b where "a" designates one ventricular channel and "b" designates the other. For each channel, the same lead and electrode are used for both sensing and stimulation. The channel interfaces 20a-b and 30 include analog-to-digital converters for digitizing sensing signal inputs from the sensing amplifiers and registers which can be written to by the microprocessor in order to output stimulation pulses, change the stimulation pulse amplitude, and adjust the gain and threshold values for the sensing amplifiers.

Figure 2:
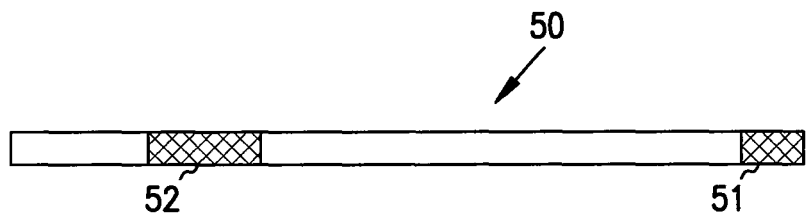
FIG. 2 shows a bipolar electrode.

The device of FIG. 1 can be configured for practicing the present invention in one embodiment by programming its microprocessor to use only one ventricular stimulation channel during any one cardiac cycle, with the ventricular electrodes 24a and 24b fixed at either separate sites in one ventricle or fixed at sites in each ventricle. A selected stimulation channel thus constitutes a pulse output configuration that can be switched by the microprocessor according to a switching algorithm as described above. By switching between the stimulation channels, the stimulation is spatially and temporally distributed over the myocardium. The device as shown has two separate ventricular stimulation channels with separate pulse generators and electrodes for each channel. Thus, the selection of a stimulation channel is effected simply by the microprocessor commanding one or the other of the channels to deliver a pulse. In another embodiment, the two electrodes 24a-b could be connected to a common pulse generator through switching circuitry that switches from one electrode to another in accordance with an output from the microprocessor. Also, instead of separate ventricular stimulation electrodes 24a-b, a single bipolar electrode 50 as shown in FIG. 2 could be used, with the device having circuitry for switching the polarity of voltage pulses output to the electrodes so that either the tip 51 or ring 52 becomes the cathode. Thus if the electrode 50 is passed into the right ventricle with the tip 51 fixed at the apex and the ring 52 residing at the base, switching the polarity of the voltage pulses enables either the apex or base to be stimulated. Similarly, if the electrode 50 is passed into the left ventricle with the ring 52 residing in the coronary sinus and the tip 51 fixed in the myocardium through a cardiac vein, both basal and apical regions of the left ventricle can be stimulated.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. Apparatus for cardiac therapy, the apparatus comprising:
   a plurality of electrodes adapted for fixation to a heart chamber;
   a control unit comprising pulse generating circuitry operable in a plurality of defined pulse output configurations, wherein each pulse output configuration activates a subset of the plurality of the electrodes, the circuitry adapted for outputting:
      a first pulse type comprising pulses to provide cardiac contractility modulating non-excitatory stimulation pulses to a selected one of the plurality of pulse output configurations in order to stimulate the heart chamber during a refractory period, wherein the pulse generating circuitry is capable of separately generating pulses to one or more of a plurality of electrodes; and
      a second pulse type comprising a defibrillation signal; and
   a switching module adapted to switch the control unit between outputting different pulse types, wherein the switching module is responsive to a sensed time delay of a depolarization occurring in at least a portion of the heart.

2. Apparatus according to claim 1, wherein the pulse generating circuitry is further adapted for outputting a third pulse type comprising a pacing signal.

3. Apparatus according to claim 2, comprising at least one thoracic sensor adapted to provide an output signal related to a cardiac output parameter;
   wherein the switching module is responsive to said output signal.

4. Apparatus according to claim 3, wherein the sensor measures a mean or a minimum heart rate over a time interval and the switching module is adapted to respond to the mean or the minimum heart rate measured over a time interval.

5. Apparatus according to claim 1, comprising at least one thoracic sensor adapted to provide an output signal related to a cardiac output parameter;
   wherein the switching module is responsive to said output signal.

6. Apparatus according to claim 5, wherein the at least one thoracic sensor senses intra-thoracic impedance.

7. Apparatus according to claim 5, wherein the thoracic sensor comprises a respiration rate detector and the switching module is responsive to the respiration rate.

8. Apparatus according to claim 5, wherein the thoracic sensor is adapted to sense a condition correlative to edema and the switching module is responsive to the condition correlative to edema.

9. Apparatus according to claim 8, wherein the thoracic sensor is adapted to sense a change in a baseline thoracic impedance associated with fluid buildup in a portion of a thorax of a subject.

10. Apparatus according to claim 9, wherein the change in the baseline thoracic impedance comprises a decrease.

11. Apparatus according to claim 9, in which the baseline portion of the thoracic impedance is less than or equal to a cutoff frequency value that is between 0.01 Hz and 0.5 Hz inclusive.

12. Apparatus according to claim 11, in which the cutoff frequency value is approximately 0.1 Hz.

13. Apparatus according to claim 1, wherein the switching module operates according to a switching algorithm.

14. Apparatus according to claim 13, wherein the switching algorithm switches the control unit intermittently.

15. Apparatus according to claim 13, wherein the switching algorithm switches the control unit substantially on a beat-to-beat basis.

16. Apparatus according to claim 13, wherein the switching algorithm switches the control unit at a specified time interval.

17. Apparatus according to claim 13, wherein the switching algorithm switches the control unit after a specified number of heart beats.

18. Apparatus according to claim 1, wherein the switching module initiates or adjusts a cardiac management therapy.

19. Apparatus according to claim 18, in which the cardiac management therapy comprises a cardiac resynchronization therapy that coordinates a spatial nature of a depolarization associated with a heart contraction in at least one heart chamber.

20. Apparatus according to claim 18, in which the cardiac management therapy comprises delivering the pulses of non-excitatory electrical energy to a portion of a heart during a refractory time period of the portion of the heart.

* * * * *